US009116107B2

(12) United States Patent
Goto et al.

(10) Patent No.: US 9,116,107 B2
(45) Date of Patent: Aug. 25, 2015

(54) X-RAY DETECTION APPARATUS FOR X-RAY FLOURESCENCE ANALYSIS

(71) Applicant: HORIBA, Ltd., Kyoto (JP)

(72) Inventors: Satoru Goto, Kyoto (JP); Tomoki Aoyama, Kyoto (JP)

(73) Assignee: HORIBA, LTD. (JP)

( * ) Notice: Subject to any disclaimer, the term of this patent is extended or adjusted under 35 U.S.C. 154(b) by 189 days.

(21) Appl. No.: 13/861,921

(22) Filed: Apr. 12, 2013

(65) Prior Publication Data

US 2013/0272498 A1    Oct. 17, 2013

(30) Foreign Application Priority Data

Apr. 12, 2012 (JP) .................................. 2012-91312

(51) Int. Cl.
*G01N 23/223* (2006.01)
*G21K 1/02* (2006.01)

(52) U.S. Cl.
CPC ................ *G01N 23/223* (2013.01); *G21K 1/02* (2013.01); *G01N 2223/076* (2013.01); *G01N 2223/316* (2013.01)

(58) Field of Classification Search
CPC .......... G01N 23/223; G01N 2223/076; G01N 2223/316; G01N 2223/317; G21K 1/02; G21K 1/025; G21K 1/04; G21K 1/043
USPC .................................................... 378/44–50
See application file for complete search history.

(56) References Cited

U.S. PATENT DOCUMENTS

| | | | | |
|---|---|---|---|---|
| 3,925,660 A * | 12/1975 | Albert | ............................. | 378/45 |
| 5,408,512 A * | 4/1995 | Kuwabara et al. | ............... | 378/45 |
| 6,028,911 A * | 2/2000 | Kawahara | ......................... | 378/44 |
| 6,038,280 A * | 3/2000 | Rossiger et al. | ................ | 378/50 |
| 6,292,532 B1 * | 9/2001 | Kawahara et al. | ............... | 378/45 |
| 6,337,897 B1 * | 1/2002 | Kawahara et al. | ............... | 378/45 |
| 6,522,718 B2 * | 2/2003 | Sato | ................................ | 378/46 |
| 6,798,863 B2 * | 9/2004 | Sato | ................................ | 378/46 |
| 6,810,106 B2 * | 10/2004 | Sato | ................................ | 378/44 |
| 6,965,663 B2 * | 11/2005 | Ohzawa | .......................... | 378/44 |
| 7,065,174 B2 * | 6/2006 | Sipila et al. | ...................... | 378/44 |
| 7,375,359 B1 * | 5/2008 | Grodzins | .......................... | 378/44 |
| 7,424,093 B2 * | 9/2008 | Fukai et al. | ...................... | 378/44 |
| 7,428,293 B2 * | 9/2008 | Fukai et al. | ...................... | 378/44 |
| 7,436,926 B2 * | 10/2008 | Matoba et al. | ................... | 378/44 |
| 7,443,951 B2 * | 10/2008 | Kenning et al. | .................. | 378/44 |
| 7,443,959 B2 * | 10/2008 | Kantonen et al. | ............. | 378/147 |
| 7,474,730 B2 * | 1/2009 | Puusaari et al. | ................ | 378/48 |
| 7,508,907 B2 * | 3/2009 | Sasayama | ........................ | 378/45 |
| 7,515,685 B2 * | 4/2009 | Iwamoto et al. | ................ | 378/44 |

(Continued)

FOREIGN PATENT DOCUMENTS

JP    2010-66121 A    3/2010

*Primary Examiner* — Allen C. Ho
(74) *Attorney, Agent, or Firm* — Cantor Colburn LLP

(57) ABSTRACT

The X-ray detection apparatus is equipped with an X-ray irradiation unit, an X-ray detector, a movable collimator and a shield for blocking X-rays. The shield blocks X-rays, which are to enter the X-ray detector directly from the X-ray irradiation unit. The shield also blocks fluorescent X-rays and scattered X-rays generated by irradiation of the collimator with X-rays. In such a manner, it is possible to prevent X-rays other than fluorescent X-rays from the sample S from being detected by the X-ray detector. The shield is joined with the collimator, so that the collimator and the shield move as a unit. It is possible to locate the shield even in a downsized X-ray detection apparatus.

10 Claims, 8 Drawing Sheets

(56) References Cited

U.S. PATENT DOCUMENTS

| | | | |
|---|---|---|---|
| 7,587,025 B2* | 9/2009 | Fukai et al. | 378/86 |
| 7,627,088 B2* | 12/2009 | Matoba et al. | 378/140 |
| 7,634,053 B2* | 12/2009 | Matoba | 378/44 |
| 7,680,248 B2* | 3/2010 | Matoba | 378/140 |
| 7,688,942 B2* | 3/2010 | Klein | 378/44 |
| 7,796,726 B1* | 9/2010 | Gendreau et al. | 378/46 |
| 7,916,834 B2* | 3/2011 | Piorek et al. | 378/44 |
| 7,970,101 B2* | 6/2011 | Sakai et al. | 378/46 |
| 8,000,439 B2* | 8/2011 | Matoba | 378/46 |
| 2013/0272497 A1* | 10/2013 | Goto et al. | 378/45 |

* cited by examiner

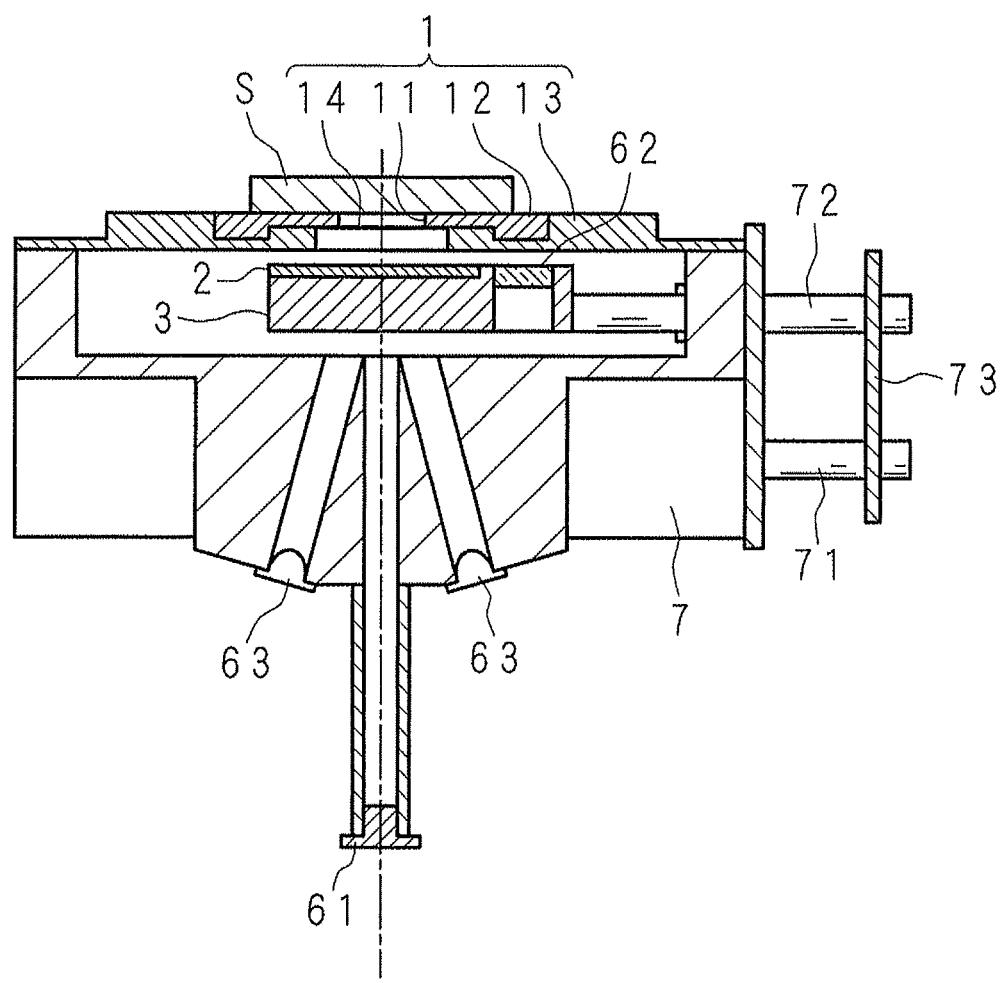
F I G. 4

X-RAY DETECTION APPARATUS FOR X-RAY FLOURESCENCE ANALYSIS

CROSS-REFERENCE TO RELATED APPLICATIONS

The present invention claims priority under 35 U.S.C. §119 to Japanese Application No. 2012-91312 filed Apr. 12, 2012, the entire content of which is incorporated herein by reference.

BACKGROUND

1. Technical Field

The present invention relates to an X-ray detection apparatus for irradiating a sample with X-rays and detecting fluorescent X-rays generated from the sample.

2. Description of Related Art

X-ray fluorescence analysis is an analytical method including steps of: irradiating a sample with X-rays; detecting fluorescent X-rays generated from the sample; and making a qualitative analysis or a quantitative analysis of elements contained in the sample according to a fluorescent X-ray spectrum. In general, an X-ray detection apparatus is provided with a collimator prepared by forming an aperture at an object which blocks X-rays in order to limit the range of X-rays by narrowing X-rays. An X-ray detection apparatus, which is equipped with a collimator including a plurality of apertures having different diameters and can move the collimator, has been developed so that the diameter of an aperture can be changed depending on the type of a sample, the purpose of analysis or the like.

In an X-ray detection apparatus, X-rays other than fluorescent X-rays generated from a sample, such as scattered X-rays or fluorescent X-rays generated at a collimator, are sometimes detected. Since detection of such X-rays causes reduction in accuracy of X-ray fluorescence analysis, it is preferable to minimize the detection of X-rays other than fluorescent X-rays generated from a sample in order to realize highly accurate X-ray fluorescence analysis. A technique disclosed in Japanese Patent Application Laid-Open No. 2010-66121 is an X-ray diffractometer equipped with a shield for blocking extra X-rays.

SUMMARY OF THE INVENTION

There is a need for downsizing of an X-ray detection apparatus in order to respond to the microminiaturization of a sample such as a circuit board. There is also a demand for downsizing of an X-ray detection apparatus in order to realize easier X-ray fluorescence analysis. In a downsized X-ray detection apparatus, an X-ray irradiation unit, an X-ray detector, a sample support unit and a collimator are located as proximally as practicable to each other. In such an X-ray detection apparatus, X-rays other than fluorescent X-rays generated from a sample, such as X-rays which are to enter the X-ray detector directly from the X-ray irradiation unit, tend to enter the X-ray detector more easily. Therefore, it is necessary to block X-rays other than fluorescent X-rays from a sample effectively.

The present invention has been made in view of such problems, and the object thereof is to provide a downsized X-ray detection apparatus which can block X-rays other than fluorescent X-rays from a sample effectively by locating a shield appropriately.

An X-ray detection apparatus according to the present invention is an X-ray detection apparatus comprising: a sample support unit; an X-ray irradiation unit configured to irradiate a sample supported by the sample support unit with X-rays; an X-ray detector configured to detect X-rays generated from the sample; and a collimator configured to narrow X-rays to be used for irradiation of the sample by the X-ray irradiation unit, characterized in that the X-ray irradiation unit and the X-ray detector are located with an exit of X-rays at the X-ray irradiation unit and an entrance of X-rays at the X-ray detector faced to a predetermined part of the sample support unit, and a shield, which blocks X-rays passing through a path linking the exit with the entrance and X-rays passing through a path linking an arbitrary part of the collimator with the entrance, is equipped.

In the present invention, an X-ray detection apparatus for detecting X-rays from a sample is equipped with an X-ray irradiation unit, an X-ray detector and a shield for blocking X-rays. The shield blocks X-rays, which are to enter the X-ray detector directly from the X-ray irradiation unit, and fluorescent X-rays and scattered X-rays generated at the collimator.

An X-ray detection apparatus according to the present invention is characterized in that the shield includes: a first shielding member configured to block X-rays passing through a path linking the exit with the entrance; and a second shielding member configured to block X-rays passing through a path linking the first shielding member and the collimator with the entrance.

In the present invention, the shield includes: a first shielding member for blocking X-rays, which are to enter the X-ray detector directly from the X-ray irradiation unit; and a second shielding member for blocking X-rays from the collimator and the first shielding member so as to prevent the X-rays from entering the X-ray detector.

An X-ray detection apparatus according to the present invention is characterized in that the collimator has a plate-like shape, and the shield is projected from both faces of the collimator.

In the present invention, the shield is projected to both face sides of the plate-like collimator. In such a structure, X-rays from both faces of the collimator are also blocked by the shield.

An X-ray detection apparatus according to the present invention is characterized in that the shield has a shape not to block an X-ray path from a sample supported by the sample support unit to the entrance.

In the present invention, the shield does not block fluorescent X-rays, which are generated at the sample and are detected by the X-ray detector. Accordingly, fluorescent X-rays of a sample are detected efficiently.

An X-ray detection apparatus according to the present invention is characterized in that the shield and the collimator are joined with each other.

In the present invention, the shield is joined with the collimator.

An X-ray detection apparatus according to the present invention is characterized in that the collimator includes a plurality of apertures configured to narrow X-rays, and the shield and the collimator can move to change an aperture through which X-rays pass.

In the present invention, the collimator can move to change an aperture for narrowing X-rays, and the collimator and the shield move as a unit.

With the present invention, a shield prevents X-rays other than fluorescent X-rays generated from a sample from entering an X-ray detector, and reduction in accuracy of X-ray fluorescence analysis is prevented, even in a state where an X-ray irradiation unit, the X-ray detector, a sample support unit and a collimator are located proximally to each other.

Consequently, the present invention has beneficial effects such that it becomes possible to downsize an X-ray detection apparatus which can be used for highly accurate X-ray fluorescence analysis.

The above and further objects and features of the invention will more fully be apparent from the following detailed description with accompanying drawings.

BRIEF DESCRIPTION OF THE SEVERAL VIEWS OF THE DRAWINGS

FIG. 4 is a schematic sectional view for illustrating the IV-IV cross section of FIG. 1;

DETAILED DESCRIPTION

The following description will explain the present invention concretely with reference to the drawings for illustrating an embodiment thereof.

Figure 1:
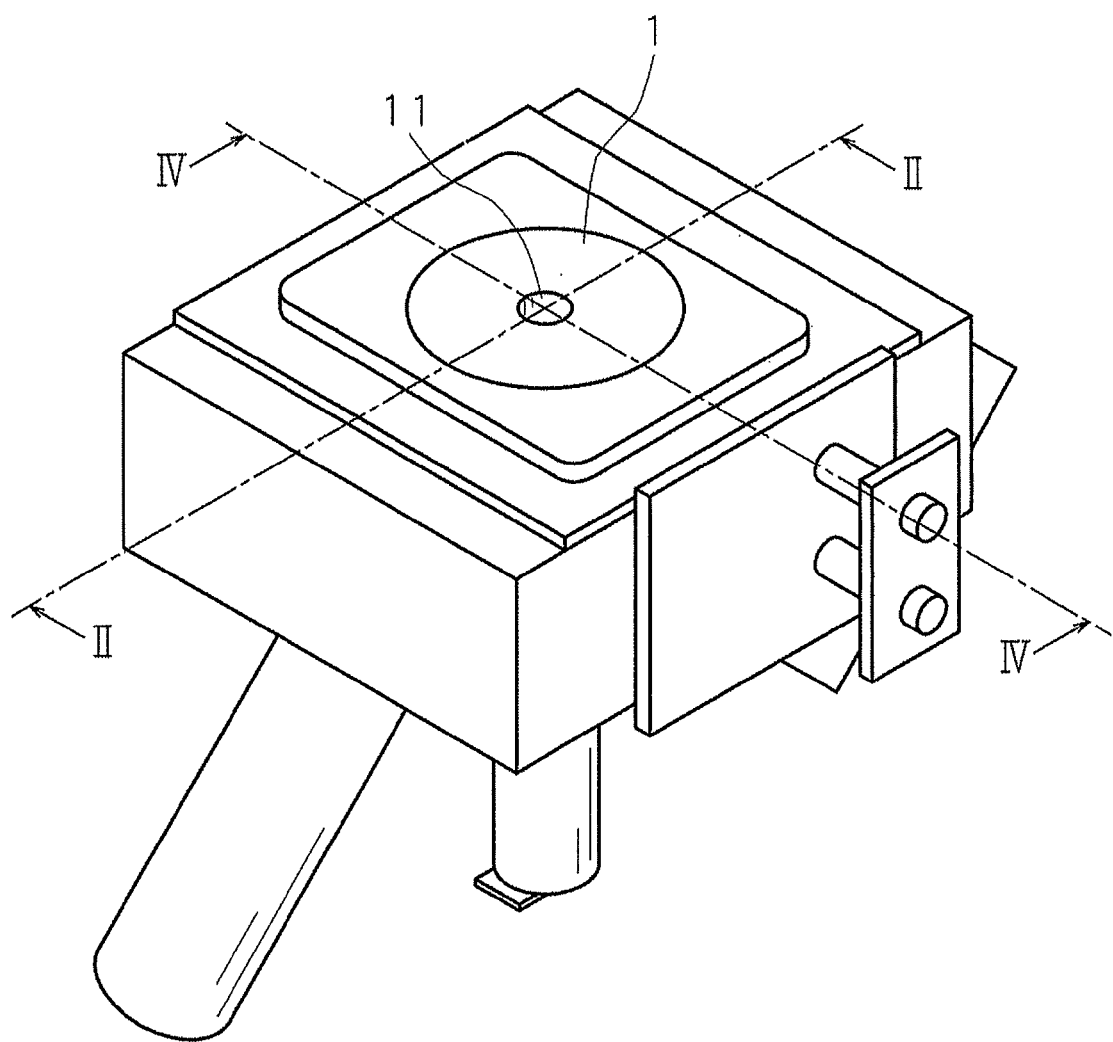
FIG. 1 is a schematic perspective view for illustrating the main structure of an X-ray detection apparatus.

FIG. 1 is a schematic perspective view for illustrating the main structure of an X-ray detection apparatus. An X-ray detection apparatus is an apparatus for making an X-ray fluorescence analysis including steps of: detecting fluorescent X-rays generated by irradiating a sample with X-rays; and measuring a fluorescent X-ray spectrum or analyzing elements contained in the sample. An X-ray detection apparatus is equipped with a sample support unit 1 for supporting a sample. The sample support unit 1 has a horizontal plate shape and supports a sample as the sample is placed thereon. The sample support unit 1 is provided with a through hole 11. A sample, which is not illustrated in FIG. 1, is placed to close the through hole 11.

Figure 2:
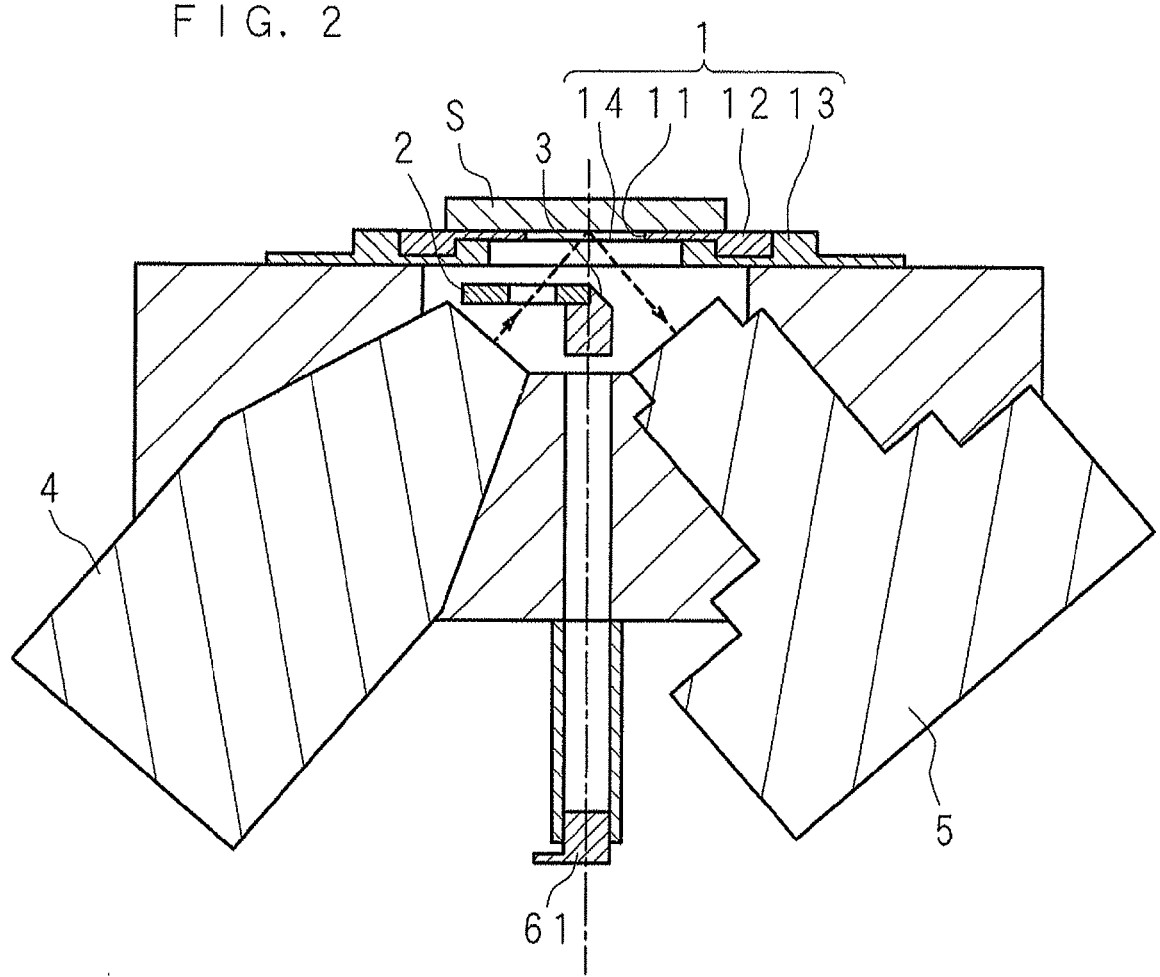
FIG. 2 is a schematic sectional view for illustrating the II-II cross section of FIG. 1.

FIG. 2 is a schematic sectional view for illustrating the II-II cross section of FIG. 1. A sample S is placed at a position to close the through hole 11 of the sample support unit 1. An X-ray irradiation unit 4 for irradiating the placed sample S with X-rays, a collimator 2 for narrowing X-rays from the X-ray irradiation unit 4, and an X-ray detector 5 for detecting fluorescent X-rays generated from the sample S are located below the sample support unit 1. Moreover, the collimator 2 is joined with a shield 3 for blocking X-rays. Although the X-ray irradiation unit 4 and the X-ray detector 5 are illustrated in FIG. 2 as cross sections simplistically, the X-ray irradiation unit 4 and the X-ray detector 5 are actually composed of a plurality of components and also include cavities therein.

The sample support unit 1 has a base unit 13 and a detachable unit 12 which can be attached to and detached from the base unit 13. The through hole 11 is formed both at the base unit 13 and the detachable unit 12, and the base unit 13 and the detachable unit 12 form a substantially plate-like shape. An X-ray transparent film 14 is spread to close the through hole 11, and the X-ray transparent film 14 is fixed between the base unit 13 and the detachable unit 12. The X-ray transparent film 14 is fixed by steps of: spreading the X-ray transparent film 14 at the through hole 11 of the base unit 13 with the detachable unit 12 detached; and attaching the detachable unit 12 to the base unit 13. The sample S is placed above the X-ray transparent film 14.

The X-ray irradiation unit 4 is located at a position to irradiate an undersurface of the sample S, which is placed on the sample support unit 1, with X-rays from obliquely below. The X-ray irradiation unit 4 is constituted of an X-ray tube and is located with an exit end of X-rays faced to the through hole 11 of the sample support unit 1. The X-ray detector 5 is located at a position to detect fluorescent X-rays radiated from the undersurface of the sample S, which is placed on the sample support unit 1, obliquely downward. The X-ray detector 5 is constituted of an X-ray detection element such as a silicon device and is located with an entrance end of fluorescent X-rays faced to the through hole 11 of the sample support unit 1. That is, the X-ray irradiation unit 4 and the X-ray detector 5 are located on the same face side of the plate-like sample support unit 1 and are located with the exit of X-rays and the entrance of fluorescent X-rays faced to a common predetermined part of the sample support unit 1. It is to be noted that there is no need to make the axis of irradiation of the X-ray irradiation unit 4 and the axis of entrance of the X-ray detector 5 overlap with each other at one point of the sample support unit 1 but it is only preferable to make the range of irradiation of X-rays from the X-ray irradiation unit 4 to the sample support unit 1 and the range of entrance of X-rays from the sample support unit 1 to the X-ray detector 5 overlap with each other. Moreover, the X-ray irradiation unit 4 and the X-ray detector 5 are located at symmetrical positions with respect to a hypothetical central axis, which is perpendicular to the plate-like sample support unit 1 and passes through the center of the through hole 11, and are located as proximally as practicable to the sample support unit 1. In FIG. 2, the hypothetical central axis is drawn with an alternate long and short dash line. The sample S is irradiated with X-rays from the X-ray irradiation unit 4, fluorescent X-rays are generated at the sample S, and the fluorescent X-rays are detected by the X-ray detector 5. In FIG. 2, X-rays from the X-ray irradiation unit 4 to be used for irradiation of the sample S and fluorescent X-rays, which are generated at the sample S and are detected by the X-ray detector 5, are drawn with dashed lines.

Figure 3:
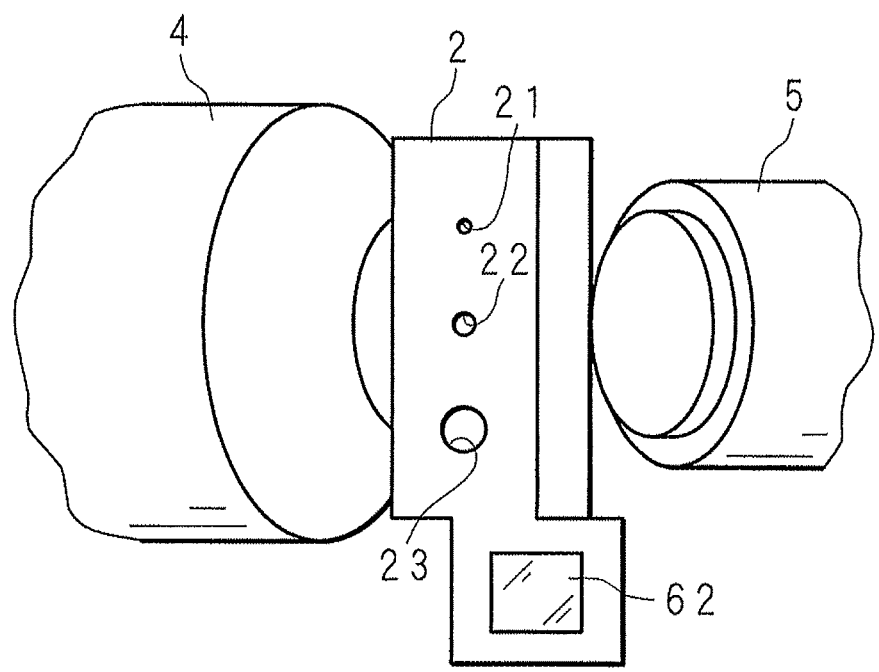
FIG. 3 is a schematic top plan view of a collimator.

The collimator 2 is located immediately below the sample support unit 1 and in an X-ray path from the X-ray irradiation unit 4 to the sample support unit 1. FIG. 3 is a schematic top plan view of the collimator 2. Actually, the sample support unit 1 is located further above the collimator 2. The collimator 2 is made of tantalum and is formed to have a plate-like shape, and a plurality of apertures 21, 22 and 23 having different diameters are formed at the collimator 2. The diameters of the apertures 21, 22 and 23 are, for example, 1.2 mm, 3 mm and 7 mm respectively. It is to be noted that the number of apertures is not limited to three but may be two or may be four or more. Moreover, there is no need to make all apertures have different diameters but it is only preferable to make at least one aperture have a diameter different from others. The apertures 21, 22 and 23 are aligned in a direction crossing a direction, in which the X-ray irradiation unit 4 and the X-ray detector 5 are aligned, in a horizontal plane.

FIG. 4 is a schematic sectional view for illustrating the IV-IV cross section of FIG. 1. The plane illustrated in FIG. 4 corresponds to a plane perpendicular to the plane illustrated in FIG. 2. In FIG. 4, a hypothetical central axis passing through the center of the through hole 11 is drawn with an alternate long and short dash line. The X-ray detection apparatus is equipped with a linear drive motor 7 functioning as a movement mechanism of the collimator 2. The linear drive motor 7 is located at a position lower than the sample support unit 1. The linear drive motor 7 is equipped with a drive shaft 71, and the drive shaft 71 is connected with a parallel shaft 72 via a connecting plate 73. The linear drive motor 7 drives the drive shaft 71 linearly, and the parallel shaft 72 reciprocates in the longitudinal direction in conjunction with the drive shaft 71. The parallel shaft 72 is connected with the collimator 2. As the parallel shaft 72 reciprocates, the collimator 2 moves along an undersurface of the sample support unit 1.

The collimator 2 can move in a direction, in which the apertures 21, 22 and 23 are aligned. The direction of movement corresponds to a direction perpendicular to the plane illustrated in FIG. 2, corresponds to the longitudinal direction of FIG. 3, and corresponds to the lateral direction of FIG. 4. As the collimator 2 moves, the apertures 21, 22 and 23 are shifted and any one of the apertures 21, 22 and 23 can be positioned in the X-ray path. When any one of the apertures 21, 22 and 23 is positioned in the X-ray path, X-rays pass through the one of the apertures 21, 22 and 23 and the sample S is irradiated with the X-rays from the X-ray irradiation unit 4. X-rays, which do not pass through the aperture, are blocked by the collimator 2. Illustrated in FIG. 3 is a state where the aperture 22 is positioned in the X-ray path. As the collimator 2 moves, an aperture through which X-rays pass is changed and the diameter of an aperture through which X-rays pass changes. As the diameter of an aperture changes, the size of X-rays to be used for irradiation of the sample S changes and the size of an analysis object part of the sample S changes. It is possible to select the size of an analysis object part of the sample S according to the objective, by selecting any one of the apertures 21, 22 and 23. The apertures 21, 22 and 23, which are located in the X-ray path from the X-ray irradiation unit 4, are positioned away from the hypothetical central axis passing through the center of the through hole 11.

Moreover, the collimator 2 is connected with a window unit 62 which allows light to pass therethrough. The window unit 62 is constituted of a transparent member such as an acrylic plate. The window unit 62 is provided at a position along a direction in which the apertures 21, 22 and 23 are aligned. An image sensor 61 such as a CCD (Charge Coupled Device) image censor or a CMOS (Complementary Metal Oxide Semiconductor) image sensor is equipped immediately below the through hole 11. The X-ray detection apparatus is also equipped with light emitting 1 devices 63 and 63 such as Light Emitting Diodes. As the parallel shaft 72 reciprocates, the window unit 62 can be positioned immediately below the through hole 11. The light emitting devices 63 and 63 emit light when the window unit 62 is positioned immediately below the through hole 11, and the emitted light passes through the window unit 62, is reflected at the sample S, passes through the window unit 62 and enters the image sensor 61. In such a manner, the sample S is photographed.

The X-ray detection apparatus is equipped with a control unit, which is not illustrated in the figures, for controlling the operations of the X-ray irradiation unit 4 and the linear drive motor 7. The control unit controls the operations of the linear drive motor 7 so as to control the position of the collimator 2. The control unit controls the position of the collimator 2 to locate the collimator 2 at one of a plurality of preset positions as needed. The plurality of positions for control include: positions to locate the apertures 21, 22 and 23 respectively in the X-ray path from the X-ray irradiation unit 4; and a position to locate the window unit 62 immediately below the through hole 11. The control unit allows X-ray irradiation by the X-ray irradiation unit 4 when any one of the apertures 21, 22 and 23 is positioned in the X-ray path from the X-ray irradiation unit 4. The control unit rejects X-ray irradiation by the X-ray irradiation unit 4 when the window unit 62 is positioned immediately below the through hole 11. It is to be noted that an X-ray detection apparatus may be constructed without including an image sensor 61, a window unit 62, and light emitting devices 63 and 63.

The X-ray detection apparatus is also equipped with a signal processing unit, which is not illustrated in the figures, for executing signal processing for X-ray fluorescence measurement. The X-ray detector 5 outputs a signal proportional to the energy of detected fluorescent X-rays to the signal processing unit, and the signal processing unit executes processing to count signals of each value and obtain the relation between energy of fluorescent X-rays detected by the X-ray detector 5 and the number of counts, that is, a fluorescent X-ray spectrum. It is to be noted that the X-ray detector 5 may be constructed to detect fluorescent X-rays separately for each wavelength. Moreover, the signal processing unit may be constructed to further execute X-ray fluorescence analysis processing of making a qualitative analysis or a quantitative analysis of elements contained in a sample on the basis of the fluorescent X-ray spectrum.

Figure 5:
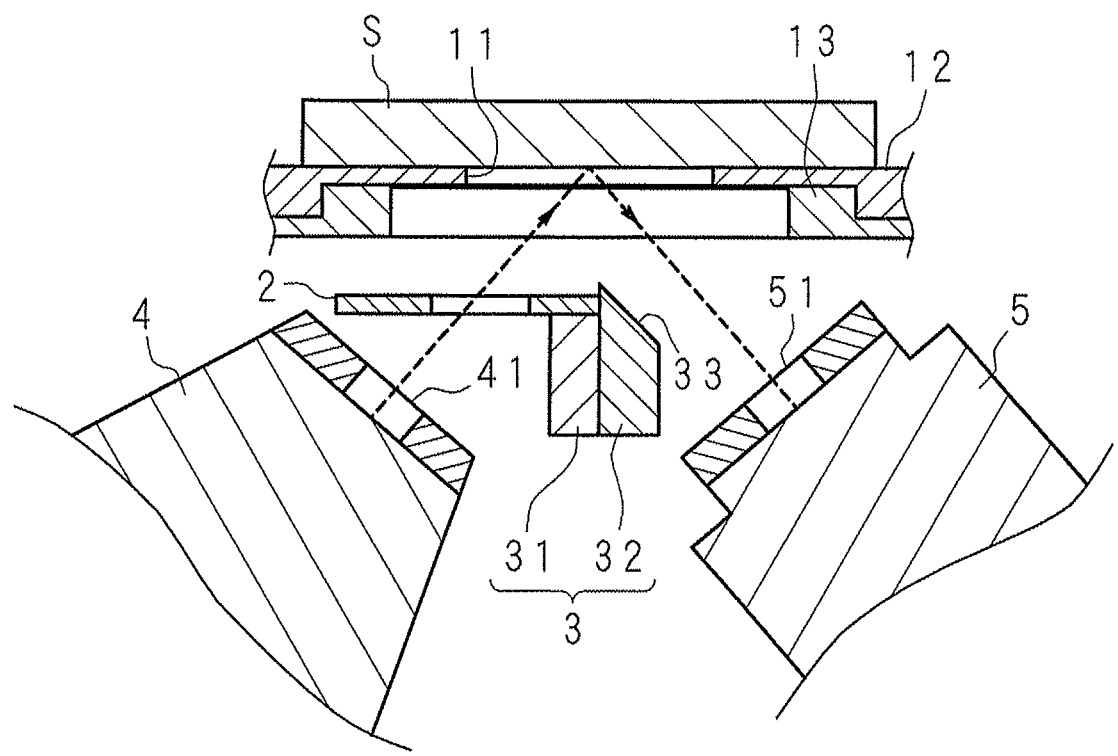
FIG. 5 is an enlarged view for illustrating the enlargement of a part including a collimator and a shield of FIG. 2.

Furthermore, the collimator 2 is joined with the shield 3 for blocking X-rays. FIG. 5 is an enlarged view for illustrating the enlargement of a part including the collimator 2 and the shield 3 of FIG. 2. The shield 3 joined with the collimator 2 moves together with the collimator 2. The shield 3 is located at an intermediate position between the X-ray irradiation unit 4 and the X-ray detector 5 in a state where any one of the apertures 21, 22 and 23 is positioned in the X-ray path from the X-ray irradiation unit 4. In particular, in such a state, the shield 3 is located at an intermediate position on a line linking an arbitrary part of an exit 41 of X-rays at the X-ray irradiation unit 4 with an arbitrary part of an entrance 51 of fluorescent X-rays at the X-ray detector 5. As the shield 3 is located at the position, X-rays passing through a path liking the exit 41 with the entrance 51 is blocked, and X-rays are prevented from entering the X-ray detector 5 directly from the X-ray irradiation unit 4.

The shield 3 is constructed by joining of a first shielding member 31 made of copper and a second shielding member 32 made of aluminum. The first shielding member 31 and the second shielding member 32 are separate bodies and are joined with each other using a screw or the like. A part, which is closer to the exit 41 of the X-ray irradiation unit 4, of parts of the shield 3 corresponds to the first shielding member 31, while a part, which is closer to the entrance 51 of the X-ray detector 5, of parts of the shield 3 corresponds to the second shielding member 32. The first shielding member 31 exists at an intermediate position on a line linking an arbitrary part of the exit 41 with an arbitrary part of the entrance 51, while the second shielding member 32 exists at an intermediate position on a line linking an arbitrary part of the first shielding member 31 and the collimator 2 with an arbitrary part of the entrance 51. The first shielding member 31 made of copper tends to absorb more intense X-rays than the second shielding member 32 made of aluminum. X-rays, which have exited from the exit 41 of the X-ray irradiation unit 4, are absorbed by the first shielding member 31. Although the absorption of X-rays causes generation of fluorescent X-rays of copper from the first shielding member 31, the fluorescent X-rays have lower intensity than the X-rays from the X-ray irradiation unit 4. The fluorescent X-rays generated from the first shielding member 31 are absorbed by the second shielding member 32. Although the second shielding member 32 also generates fluorescent X-rays, the fluorescent X-rays have further lower intensity and attenuate before entering the entrance 51. The effect of the fluorescent X-rays from the second shielding member 32 on X-ray fluorescence analysis is significantly smaller than that of the X-rays from the X-ray irradiation unit 4.

Moreover, the shield 3 is provided at an intermediate position on a line linking an arbitrary part of the collimator 2 with an arbitrary part of the entrance 51. In a state where any one of the apertures 21, 22 and 23 is positioned in the X-ray path from the X-ray irradiation unit 4, the shield 3 exists between the entire collimator 2 and the entrance 51. The collimator 2 is irradiated with X-rays, which do not pass through the aperture, and fluorescent X-rays and scattered X-rays are generated from the collimator 2. To prevent the fluorescent X-rays and scattered X-rays from entering the X-ray detector 5, the first shielding member 31 blocks a part of X-rays generated from the collimator 2 and the second shielding member 32 blocks X-rays, which have not been blocked by the first shielding member 31, of the X-rays generated from the collimator 2. In such a manner, X-rays from the collimator 2 are blocked by the shield 3, and are prevented from entering the X-ray detector 5. Consequently, X-rays other than fluorescent X-rays generated from the sample S is prevented from entering the X-ray detector 5 effectively, and reduction in accuracy of X-ray fluorescence analysis is prevented. The X-ray detection apparatus can be used for highly accurate X-ray fluorescence analysis.

The shield 3 is connected with an end, which is closer to the X-ray detector 5, of the plate-like collimator 2. Since the entrance 51 of the X-ray detector 5 is positioned closer to an undersurface than an upper surface of the collimator 2, the shield 3 is projected below the collimator 2 in order to block X-rays from the collimator 2 to the entrance 51. Moreover, the second shielding member 32 has a part projected above the collimator 2. Since the second shielding member 32 is projected to the upper and lower sides of the collimator 2, the shield 3 reliably blocks not only X-rays exiting from the collimator 2 to the lower side but also X-rays exiting from the collimator 2 to the upper side. This effectively prevents X-rays other than fluorescent X-rays generated from the sample S from entering the X-ray detector 5. The shield 3 is not provided below the window unit 62.

The material of the collimator 2 is tantalum, which generates fluorescent X-rays having higher energy than copper that is the material of the first shielding member 31. Copper which is the material of the first shielding member 31 generates fluorescent X-rays having higher energy than aluminum which is the material of the second shielding member 32. In comparison with the energy of fluorescent X-rays generated from the collimator 2 which is mainly subjected to X-rays from the X-ray irradiation unit 4, the energy of fluorescent X-rays generated from the first shielding member 31 which is subjected to X-rays next is lower, and the energy of fluorescent X-rays generated from the second shielding member 32 is further lower. In a path of X-rays other than fluorescent X-rays from the sample S to enter the X-ray detector 5, energy of X-rays attenuates sequentially and X-rays are blocked effectively. It is to be noted that the materials of the collimator 2, the first shielding member 31 and the second shielding member 32 may be changed to other combinations, as long as fluorescent X-rays generated from the collimator 2 have the highest energy and fluorescent X-rays generated from the second shielding member 32 have the lowest energy.

Moreover, an upper end part 33 of the second shielding member 32 has a shape not to block a path of fluorescent X-rays from the sample S to the entrance 51 of the X-ray detector 5. Specifically, the upper end part 33 has a shape to avoid a path linking an upper end of the through hole 11 with the entrance 51. Therefore fluorescent X-rays from the sample S enter the entrance 51 efficiently and are detected by the X-ray detector 5. Moreover, there is no need to provide a structure for fixing the shield 3 separately from the collimator 2, since the shield 3 is joined with the collimator 2 to move together with the collimator 2. This makes it possible to locate the shield 3 for blocking X-rays effectively even in a state where the X-ray irradiation unit 4, the X-ray detector 5, the sample support unit 1 and the collimator 2 are positioned as proximally as practicable to each other. Since it is possible to locate the shield 3 even in a downsized X-ray detection apparatus, it becomes possible to downsize an X-ray detection apparatus which can be used for highly accurate X-ray fluorescence analysis.

Figure 6:
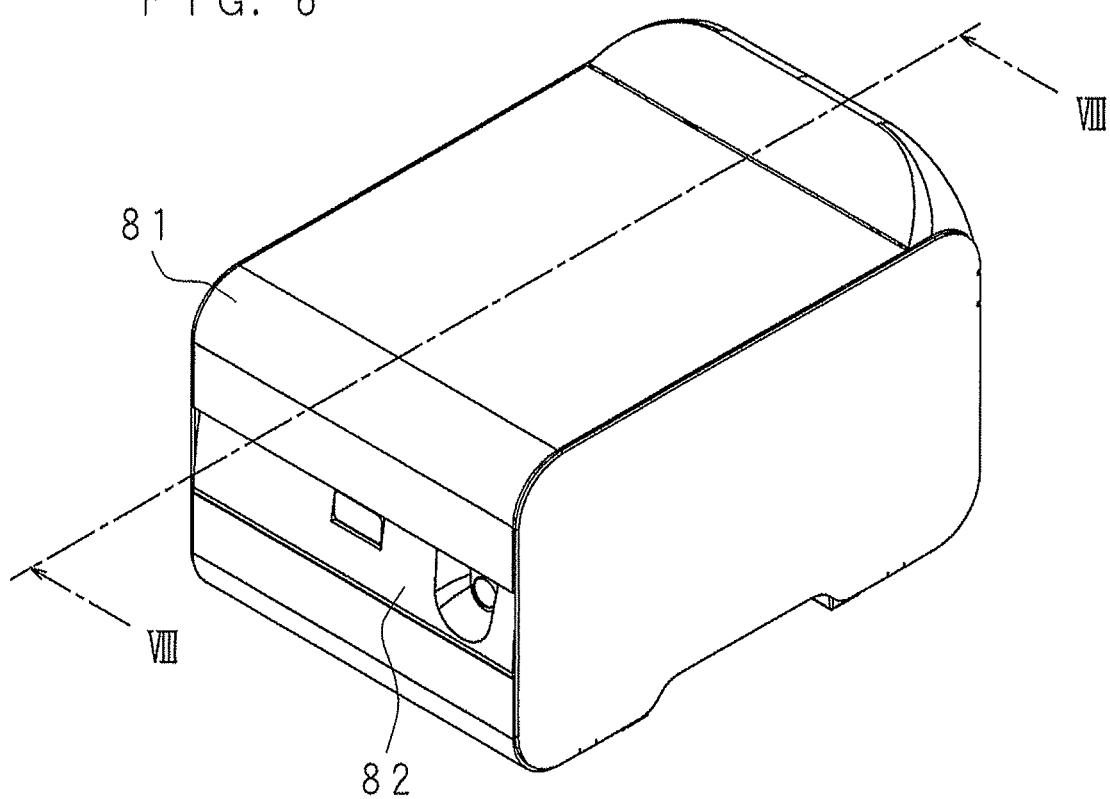
FIG. 6 is a perspective view for illustrating the appearance of an X-ray detection apparatus.
Figure 7:
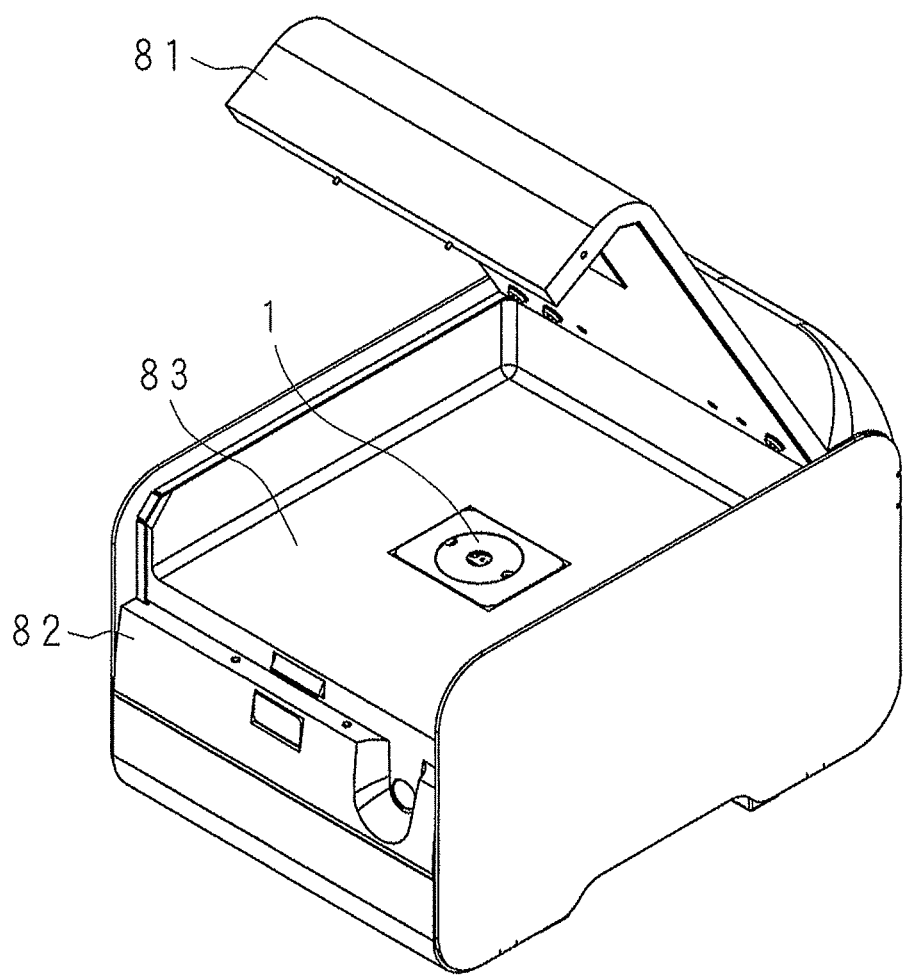
FIG. 7 is a perspective view for illustrating an X-ray detection apparatus in a state where a cover part is open.

FIG. 6 is a perspective view for illustrating the appearance of an X-ray detection apparatus. A main part of the X-ray detection apparatus is held in a case together with other parts, which are not illustrated in the figures, such as a power supply unit, and a part of the case is formed of a resin member 82. The case is covered with a cover part 81 made of metal. FIG. 7 is a perspective view for illustrating an X-ray detection apparatus in a state where the cover part 81 is open. The cover part 81 has a shape in which an end part of a plate is curved, and the curved end part functions as a movable end. An end part opposite to the curved end part functions as a connected end to be connected with the case by a hinge, and the cover part 81 can be opened and closed to the case by the operations of the hinge. In a state where the cover part 81 is closed, the movable end of the cover part 81 is fixed at the case with a stopper. The X-ray detection apparatus is provided with a plane part 83, which is constituted of an upper surface of the resin member 82. An upper side of the plane part 83 is covered with the cover part 81 in a state where the cover part 81 is closed, while an upper side of the plane part 83 is open in a state where the cover part 81 is opened. An opening is formed at the plane part 83, and the sample support unit 1 is located at the position of the opening. An upper surface of the detachable unit 12 is substantially in plane with a surface of the plane part 83. A main part of the X-ray detection apparatus other than the sample support unit 1 is located at a position below the plane part 83.

Figure 8:
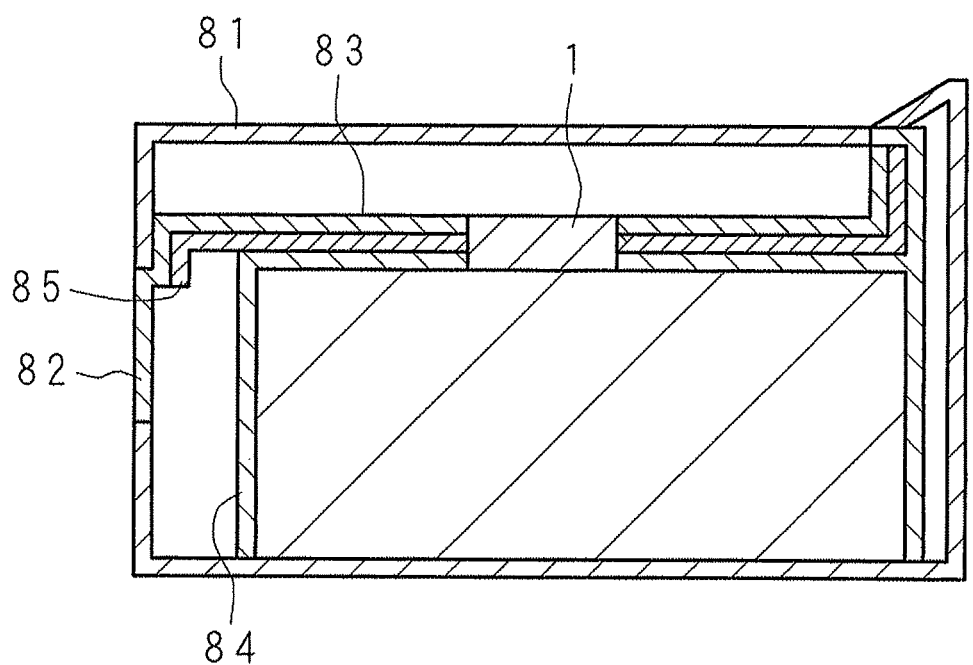
FIG. 8 is a schematic sectional view for illustrating the VIII-VIII cross section of FIG. 6.

FIG. 8 is a schematic sectional view for illustrating the VIII-VIII cross section of FIG. 6. A metal plate 85 is equipped at a position lower than the plane part 83. The metal plate 85 is located along the rear side of the resin member 82. The metal plate 85 has an opening at a part where the sample support unit 1 is located. A front end part of the metal plate 85 has a shape curving downward, and a back end part of the metal plate 85 has a shape curving upward. A shield box 84 made of metal is provided inside the case, and a main part of the X-ray detection apparatus other than the sample support unit 1, which is not illustrated in FIG. 8, is located inside the shield box 84. The upper side and the lateral sides of a main part of the X-ray detection apparatus other than the sample support unit 1 are surrounded by the shield box 84 made of metal. This makes X-rays to the upper side and to the lateral sides blocked by the shield box 84. X-rays which have leaked to the upper side of the sample support unit 1 are blocked by the cover part 81 made of metal. Moreover, X-rays radiated from the upper side of the sample support unit 1 to the front direction of the X-ray detection apparatus are blocked by end parts of the cover part 81 and the metal plate 85. For closing the cover part 81, the movable end of the cover part 81 overlaps with the metal plate 85 in the front direction. This makes X-rays radiated from the upper side of the sample support unit 1 to the front direction of the X-ray detection apparatus collide with any one of end parts of the cover part 81 or the metal plate 85 and blocked reliably. With such a structure, the X-ray detection apparatus can block X-rays reliably and ensure safety even though the case includes the resin member 82. Since a part of the case is made of resin, weight saving of an X-ray detection apparatus can be realized. Weight saving of an X-ray detection apparatus can improve the portability and the convenience of the X-ray detection apparatus.

As this invention may be embodied in several forms without departing from the spirit of essential characteristics thereof, the present embodiment is therefore illustrative and not restrictive, since the scope of the invention is defined by the appended claims rather than by the description preceding them, and all changes that fall within metes and bounds of the claims, or equivalence of such metes and bounds thereof are therefore intended to be embraced by the claims.

What is claimed is:

1. An X-ray detection apparatus comprising:
   a sample support unit;
   an X-ray irradiation unit, which is located with an exit of X-rays faced to a predetermined part of the sample support unit, structured to irradiate a sample supported by the sample support unit with X-rays;
   an X-ray detector, which is located with an entrance of X-rays faced to the predetermined part of the sample support unit, structured to detect fluorescent X-rays generated from the sample;
   a collimator structured to narrow X-rays to be used for irradiation of the sample by the X-ray irradiation unit; and
   a shield disposed to block X-rays emitted from the X-ray irradiation unit from passing through a path linking the exit of the X-ray irradiation unit with the entrance of the X-ray detector in a straight line, and the shield being further disposed to block fluorescent X-rays generated by the collimator or scattered X-rays generated by the collimator from passing through a path linking an arbitrary part of the collimator with the entrance of the X-ray detector in a straight line.

2. The X-ray detection apparatus according to claim 1, wherein the shield includes:
   a first shielding member configured to block X-rays passing through a path linking the exit with the entrance; and
   a second shielding member configured to block X-rays passing through a path linking the first shielding member and the collimator with the entrance.

3. The X-ray detection apparatus according to claim 2, wherein the collimator has a plate-like shape, and the shield is projected from both faces of the collimator.

4. The X-ray detection apparatus according to claim 2, wherein the shield has a shape not to block an X-ray path from a sample supported by the sample support unit to the entrance.

5. The X-ray detection apparatus according to claim 2, wherein the shield is joined with the collimator.

6. The X-ray detection apparatus according to claim 5, wherein the collimator includes a plurality of apertures configured to narrow X-rays, and the shield and the collimator move to change an aperture through which X-rays pass.

7. The X-ray detection apparatus according to claim 1, wherein the collimator has a plate-like shape, and the shield is projected from both faces of the collimator.

8. The X-ray detection apparatus according to claim 1, wherein the shield has a shape not to block an X-ray path from a sample supported by the sample support unit to the entrance.

9. The X-ray detection apparatus according to claim 1, wherein the shield is joined with the collimator.

10. The X-ray detection apparatus according to claim 9, wherein the collimator includes a plurality of apertures configured to narrow X-rays, and the shield and the collimator move to change an aperture through which X-rays pass.

* * * * *